United States Patent [19]
Webb

[11] Patent Number: 5,718,708
[45] Date of Patent: Feb. 17, 1998

[54] OPHTHALMIC INSTRUMENT FOR REMOVING FOREIGN OBJECTS

[76] Inventor: Nicholas J. Webb, 5370 Basel Dr., P.O. Box 831, Wrightwood, Calif. 92397

[21] Appl. No.: 813,048

[22] Filed: Mar. 7, 1997

Related U.S. Application Data

[63] Continuation of Ser. No. 625,161, Apr. 1, 1996, abandoned.

[51] Int. Cl.[6] .................................................... A61F 9/00
[52] U.S. Cl. ........................ 606/107; 606/167; 606/162
[58] Field of Search ................................. 606/107, 1, 4, 606/13, 15, 79, 84, 131, 162, 167, 160, 161, 168; 604/116

[56] References Cited

U.S. PATENT DOCUMENTS

| | | | |
|---|---|---|---|
| 872,567 | 12/1907 | Langstaff | 606/160 |
| 3,583,390 | 6/1971 | Jascalevich | 606/170 |
| 3,670,733 | 6/1972 | Carlisle | 606/172 |
| 3,798,688 | 3/1974 | Wasson | 30/357 |
| 4,126,136 | 11/1978 | Auth et al. | 606/16 |
| 5,116,347 | 5/1992 | Butler | 606/131 |
| 5,176,694 | 1/1993 | Price | 606/162 |
| 5,203,865 | 4/1993 | Siepser | 606/166 |
| 5,217,477 | 6/1993 | Lager | 606/166 |
| 5,219,350 | 6/1993 | Emerson et al. | 606/107 |
| 5,299,893 | 4/1994 | Salyer et al. | 606/79 |
| 5,324,306 | 6/1994 | Makower et al. | 606/213 |
| 5,352,233 | 10/1994 | Anis | 606/167 |
| 5,431,665 | 7/1995 | Li | 606/131 |

OTHER PUBLICATIONS

Storz surgical instruments catalog, pp. 38, 179, and 180.

*Primary Examiner*—Robert A. Hafer
*Assistant Examiner*—Justine R. Yu
*Attorney, Agent, or Firm*—Jack Lo

[57] ABSTRACT

An ophthalmic instrument for removing foreign objects from an ocular surface includes a multi-purpose tool head attached at an angle to the end of a handle. The generally flat tool head includes a main body and an upwardly angled distal tip. A pair of side scoops are arranged on the sides of the main body, and an omnidirectional plane is arranged between the side scoops. A V-shaped notch with a sharply beveled front edge is arranged on one side of the main body. The upturned distal tip is usable for prying out partially embedded objects. The V-shaped notch is usable for securely engaging both sides of an object and gently rocking it loose. The side scoops and the plane are usable for scooping or rocking loose objects. A graduated scale is provided on the tool head for measuring the size of the foreign objects. Accordingly, the present ophthalmic instrument provides several tools for removing foreign objects of different sizes, shapes, and consistencies. Additionally, the tool head is made of an optically clear plastic, so that it does not obscure the surgical field.

19 Claims, 3 Drawing Sheets

OPHTHALMIC INSTRUMENT FOR REMOVING FOREIGN OBJECTS

This application is a continuation of prior application Ser. No. 08/625,161; filed on Apr. 1, 1996, now abandoned.

BACKGROUND OF THE INVENTION

1. Field of the Invention

This invention relates generally to ophthalmic instruments, specifically to an ophthalmic instrument for removing foreign objects from an ocular surface.

2. Prior Art

Eye injuries are often caused by small foreign objects that are accidentally introduced onto the ocular surface. For example, wood, plastic, or metal debris are often propelled into the eyes of workers not using eye protection. In vehicular collisions, bits of window glass often fly into the occupants' eyes. Also, sand is often blown into people's eyes by wind. Such foreign objects are often simply adhered to the ocular surface, and may be easily washed off with water. However, they are sometimes partially embedded, so that they must be carefully removed to avoid further damage to the eye.

Optometrists, ophthalmologists, and other healthcare professionals use a variety of instruments for removing foreign objects from the ocular surface. Storz, a medical instruments manufacturer, offers a variety of suitable instruments, including curettes and spuds, which are scoops and spades, respectively. Also, U.S. Pat. No. 5,219,350 to Emerson et al. (1993) discloses an ophthalmic instrument that includes a handle with an illuminated distal end for accepting a variety of tool heads, including spuds and monofilament loops.

However, most prior art instruments, such as loops and curettes, drag foreign objects across the ocular surface, which may cause additional damage. Loops also have a tendency to push debris back into a wound. Typical instruments are much larger than most foreign objects encountered on the eye, so that they are cumbersome to handle, and are unsuitable for manipulating the tiny debris. Each prior art instrument is shaped to perform a single function, so that several instruments are typically required for dislodging and removing debris of different shapes during each procedure. The physician must look away, put down an instrument, pick up another, and refocus on the surgical field. Having to constantly swap instruments is inconvenient and cumbersome, and having to stock a variety of instruments is expensive. All prior art instruments are made of opaque materials, such as steel, so that even small ones may obscure the surgical field enough to hinder the procedure. Furthermore, all prior art instruments require sterilization, which is time consuming and increases operating costs.

OBJECTS OF THE INVENTION

Accordingly an object of the present invention is to provide an ophthalmic instrument for safely removing foreign objects from an ocular surface without causing further damage.

Another object of the present invention is to provide an ophthalmic instrument that provides several different tools specialized for removing foreign objects of different sizes, shapes, and consistencies.

Another object of the present invention is to provide an ophthalmic instrument that is transparent so as not to obscure the surgical field.

Another object of the present invention is to provide an ophthalmic instrument that is provided in a sterile, ready-to-use package.

Another object of the present invention is to provide an ophthalmic instrument that is ergonomically shaped for comfortable and precise handling.

Yet another object of the present invention is to provide an ophthalmic instrument that is usable for measuring the size of the foreign objects on the ocular surface.

Still another object of the present invention is to provide an ophthalmic instrument is inexpensive and disposable.

Further objects of the present invention will become apparent from a consideration of the drawings and ensuing description.

SUMMARY OF THE INVENTION

An ophthalmic instrument for removing foreign objects from an ocular surface includes a generally flat, multi-purpose tool head attached at an angle to the end of a handle. The tool head includes a main body, and a pointed distal tip that is angled upwardly relatively to the main body. A pair of sharply beveled side scoops are arranged on the sides of the main body, and an annular plane is arranged between the scoops. A V-shaped notch with a sharply beveled front edge is arranged on one side of the main body. The distal tip is usable for prying loose partially embedded foreign objects. The V-shaped notch is usable for engaging both sides of a foreign object and gently rocking it loose. The side scoops and the plane are usable for scooping or prying loose objects. All the tools lift or scoop foreign objects upwardly without dragging them to avoid further damage to the eye. The tool head also includes a scale for measuring the size of the foreign objects. The tool head is made of an optically clear rigid plastic, so that it does not obscure the surgical field.

DETAILED DESCRIPTION OF THE INVENTION

Figure 1:
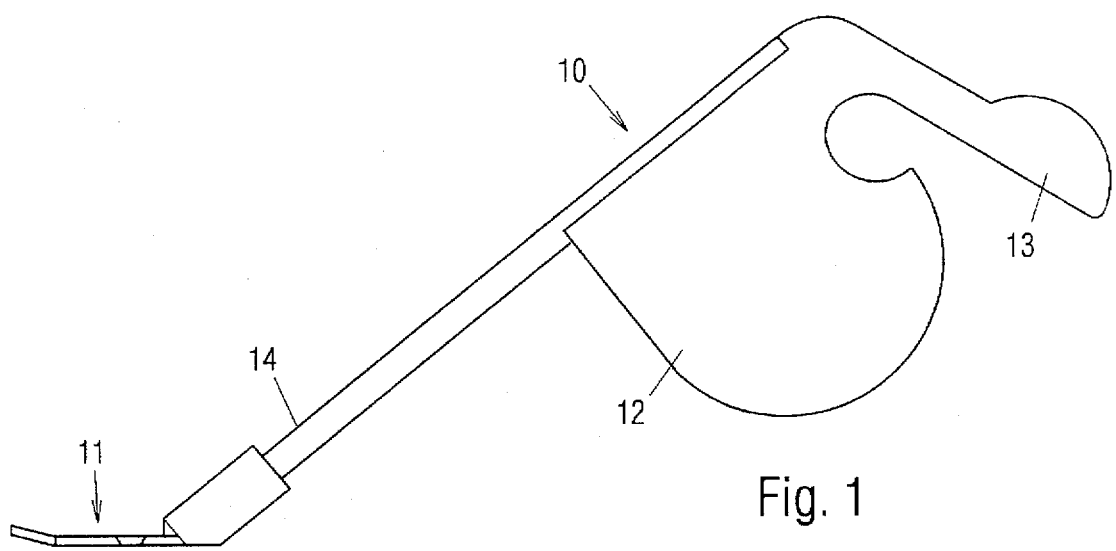
FIG. 1 is a side view of an ophthalmic instrument in accordance with a preferred embodiment of the invention.

In accordance with a preferred embodiment of the invention shown in the side view of FIG. 1, an ophthalmic instrument for removing foreign objects from an ocular surface includes a handle 10 and a multi-purpose tool head 11. Handle 10 includes ergonomically shaped finger grips 12 and 13 for convenient and precise handling, and an elongated shaft 14. Tool head 11 is attached to the distal end of shaft 14 at a 140 degree angle between shaft 14 and the top surface of tool head 11.

Figure 2:
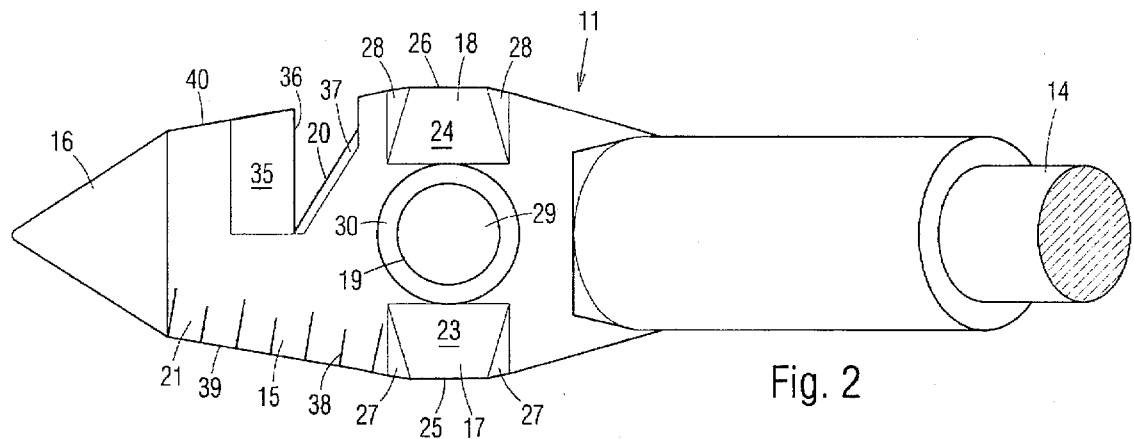
FIG. 2 is an enlarged top view of a tool head of the ophthalmic instrument.
Figure 3:
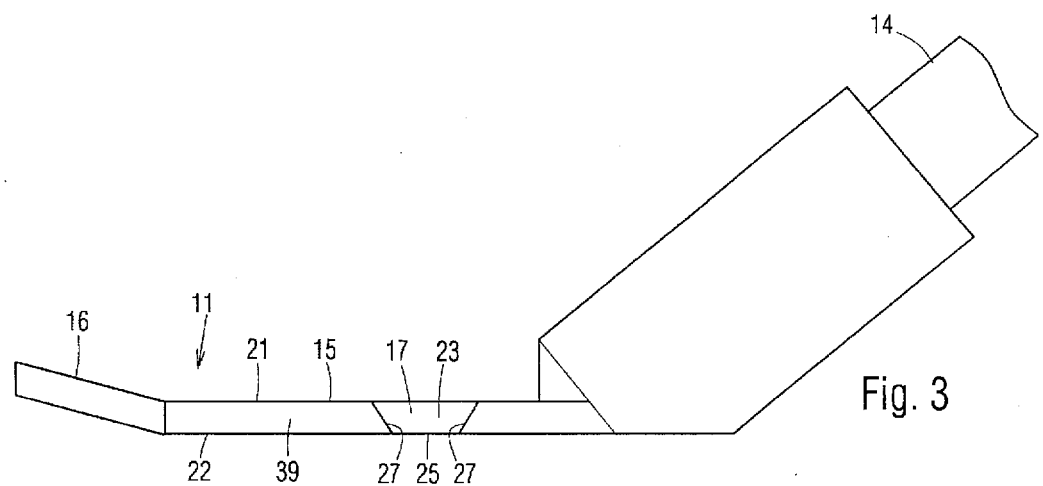
FIG. 3 is an enlarged side view of the tool head.
Figure 4:
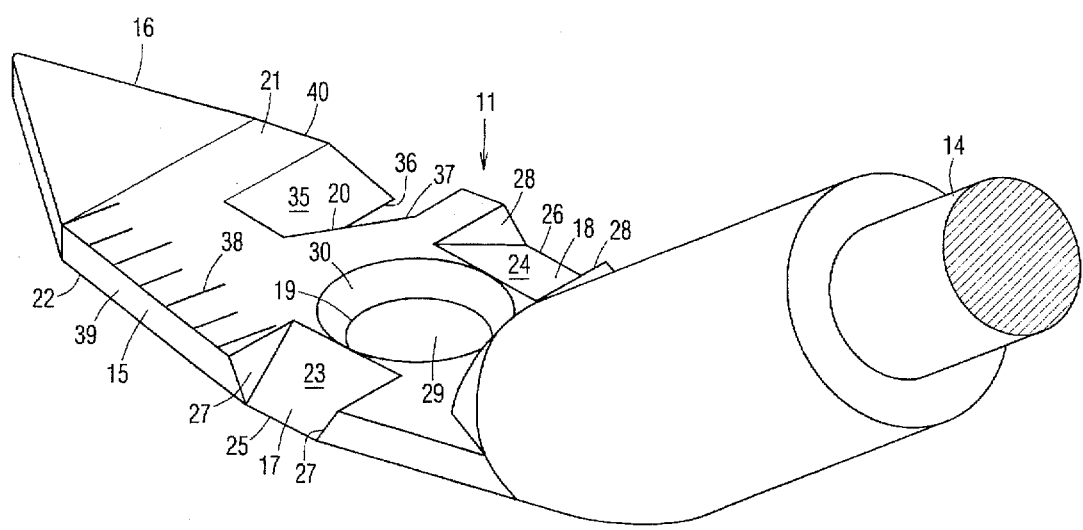
FIG. 4 is an enlarged side perspective view of the tool head.

Tool head 11 is shown enlarged in FIGS. 2–4. It includes a main body 15, and a pointed tip 16, which has a slightly rounded distal point for safety. Tip 16 is angled upwardly 15 degrees with respect to main body 15. Tool head 11 includes flat top and bottom surfaces 21 and 22, respectively, and opposite side edges 39 and 40. The portion of bottom surface 22 under tip 16 is provided with a slightly abrasive texture (not shown). Tool head 11 also includes a pair of opposite side scoops 17 and 18 arranged on sides 39 and 40, respectively, an omnidirectional plane 19 arranged between side scoops 17 and 18, and a V-shaped notch 20 arranged on side 40 between side scoop 18 and tip 16. A measuring scale 38 is arranged along side 39, and includes 0.5 mm graduations. Tip 16 is the forward end of tool head 11.

Side scoops 17 and 18 are defined by sharply beveled top surfaces 23 and 24, respectively, that form sharp, straight leading edges 25 and 26, respectively, and raised sides 27 and 28, respectively. Plane 19 is defined by a circular hole 29 extending through main body 15. Hole 29 includes an annular wall 30 that is tapered inwardly from top to bottom. V-shaped notch 20 is defined by a sharply beveled front side 35, which forms a blade 36, and a slightly beveled rear side 37.

The angle of tool head 11 relative to shaft 14 enables bottom surface 22 to be positioned flat against the ocular surface while handle 10 is held at a comfortable angle, and also enables tool head 11 to be easily positioned on patients with deep brows. Upturned tip 16 is usable for levering substantially embedded foreign objects from the ocular surface. V-shaped notch 20 is usable for engaging both sides of an object such as a splinter or a wire, gently rocking it loose, and safely scooping it up with blade 36. Omnidirectional plane 19 is usable for being positioned around a foreign object, and safely lifting it by pulling tool head 11 in any horizontal direction. The lower rim of plane 19 is flush with bottom surface 22, so that it will not penetrate the ocular surface. Opposite side scoops 17 and 18 are usable for scooping up foreign objects with sideways movement in either direction without requiring repositioning of the instrument. The abrasive bottom surface of tip 16 is usable for sanding away minute particles. Scale 38 is usable for conveniently measuring the size of the foreign objects for recording in patient files.

All the tools pull or scoop debris upwardly and safely from the ocular surface, so that they will not cause further damage. Thus tool head 11 provides several tools specialized for removing foreign objects of different sizes, shapes, and consistencies. It can safely and conveniently remove foreign objects from an ocular surface, without requiring the physician to look away and reach for other tools.

Tool head 11 is about 8 mm long, so that the tools provided thereon are correspondingly smaller, and therefore appropriately sized for the foreign objects typically found on eyes. Tool head 11 is made of an optically clear, FDA approved rigid plastic, so that it will not obscure the surgical field. It is provided in a sterile, ready-to-use package (not shown). The present ophthalmic instrument is easily producible by injection molding, so that it is inexpensive enough to be used as a single-use, disposable instrument.

SUMMARY, SUBSTITUTES, AND SCOPE

Accordingly, I have provided an ophthalmic instrument that is usable for safely lifting foreign objects from an ocular surface without causing further damage. It can singly perform a variety of tasks necessary for safely and quickly removing foreign objects of different sizes, shapes, and consistencies from an ocular surface, without requiring a physician to look away and reach for other tools. It is ergonomically shaped for convenient and precise handling. It includes a transparent tool head that does not obscure the surgical field. It is usable for measuring the size of the foreign objects. It is provided in a sterile package as an inexpensive, ready-to-use, disposable instrument.

Although the above descriptions are specific, they should not be considered as limitations on the scope of the invention, but only as examples of the embodiments. Many substitutes and variations are possible within the teachings of the invention. For example, the shape of the handle may be changed. The measuring scale may be arranged on other parts of the instrument, such as along the handle, and it may be provided with graduations of other sizes. The angle between the tool head and the handle may be changed. The angle between the tip and the main body of the tool head may also be changed. The tool head may be made of other materials. The plane may be rectangular instead of circular. The tip may be of other shapes. The rear edge of the V-shaped notch may also be sharply beveled. Instead of being upturned, the pointed tip of the tool head may be aligned with the main body. The V-shaped notch may be positioned on the other side of the main body, or two notches may be provided on both sides thereof. More or fewer tools may be provided on the tool head. The size of the tool head may be altered. The instrument may be used for scooping up debris from other parts of the body, and it may also be used for non-medical applications. Therefore, the scope of the invention should be determined by the appended claims and their legal equivalents, not by the examples given.

I claim:

1. An ophthalmological surgical instrument, comprising:
   an elongated handle;
   a tool head having a rear end attached to a distal end of said handle, said tool head having a top surface and a bottom surface, opposite side edges, and a forward distal tip adapted for prying debris from a surgical surface; and
   a pair of opposite side scoops extending inwardly from said side edges of said tool head, each of said side scoops comprising a pair of opposite sides extending downwardly from said top surface of said tool head, and a beveled surface connecting said opposite sides, said beveled surface slanting inwardly and upwardly from said bottom surface of said tool head and forming a leading edge along said bottom surface, said bottom surface of said tool head being adapted to be positioned flat on said surgical surface, and said side scoops are adapted for scooping up said debris from said surgical surface by moving said tool head sideways to either side, said opposite sides of each of said side scoops being generally orthogonal to a corresponding side edge of said tool head for facilitating guiding said debris up onto said beveled surface.

2. The ophthalmological surgical instrument of claim 1 wherein said tool head is attached to said handle at an obtuse angle between said top surface and said handle.

3. The ophthalmological surgical instrument of claim 1 wherein said forward distal tip is angled upwardly relative to said top surface of said tool head.

4. The ophthalmological surgical instrument of claim 1 wherein said tool head is made of a transparent material for enabling a user to see said surgical surface under said tool head when said bottom surface of said tool head is positioned flat on said surgical surface.

5. The ophthalmological surgical instrument of claim 1, further including a plane arranged on said tool head, said plane comprising a hole extending through said top surface and said bottom surface, said hole including a wall tapered inwardly from top to bottom.

6. The ophthalmological surgical instrument of claim 1, further including a V-shaped notch arranged along one of said side edges of said tool head and adapted for prying said debris from said surgical surface.

7. The ophthalmological surgical instrument of claim 6 wherein said V-shaped notch includes a sharply beveled front edge that forms a rear facing blade, said V-shaped notch also includes a rear edge.

8. The ophthalmological surgical instrument of claim 1, further including a measuring scale arranged on said tool head, said scale being adapted for conveniently measuring said debris on said surgical surface.

9. An ophthalmological surgical instrument, comprising:

an elongated handle;

a tool head having a rear end attached to a distal end of said handle, said tool head having a top surface and a completely flush bottom surface, opposite side edges, and a distal tip adapted for prying debris from a surgical surface;

a V-shaped notch extending inwardly from one of said side edges of said tool head, said V-shaped notch comprising a forward edge generally perpendicular to said one of said side edges of said tool head, and a rear edge at an acute angle to said forward edge, said forward edge of said V-shaped notch being tapered downwardly forming a sharp edge along said bottom surface of said tool head, said V-shaped notch having an opening flush with said one of said side edges of said tool head, said bottom surface of said tool head and said V-shaped notch being adapted to be positioned flat on said surgical surface, said V-shaped notch being adapted for prying said debris from said surgical surface; and said tool head further including a plane, said plane comprising a hole extending through said top surface and said bottom surface, said hole including a wall tapered inwardly from top to bottom.

10. The ophthalmological surgical instrument of claim 9 wherein said tool head is attached to said handle at an obtuse angle between said top surface and said handle.

11. The ophthalmological surgical instrument of claim 9 wherein said tool head is made of a transparent material for enabling a user to see said surgical surface under said tool head when bottom surface of said tool head is positioned flat on said surgical surface.

12. The ophthalmological surgical instrument of claim 9 wherein said forward edge of said V-shaped notch is sharply beveled so as to form a rear facing blade.

13. The ophthalmological surgical instrument of claim 9, further including a measuring scale arranged on said tool head, said scale being adapted for conveniently measuring said debris on said surgical surface.

14. An ophthalmological surgical instrument, comprising:

an elongated handle;

a tool head having a rear end attached to a distal end of said handle, said tool head having a top surface and a bottom surface, opposite side edges, and a forward distal tip adapted for prying debris from a surgical surface;

a pair of opposite side scoops extending inwardly from said side edges of said tool head, each of said side scoops comprising a pair of opposite sides extending downwardly from said top surface of said tool head, and a beveled surface connecting said opposite sides, said beveled surface slanting inwardly and upwardly from said bottom surface of said tool head and forming a leading edge along said bottom surface, said bottom surface of said tool head being adapted to be positioned flat on said surgical surface, and said side scoops are adapted for scooping up said debris from said surgical surface by moving said tool head sideways to either side, said opposite sides of each of said side scoops being generally orthogonal to a corresponding side edge of said tool head for facilitating guiding said debris up onto said beveled surface; a V-shaped notch arranged on said tool head, said V-shaped notch being adapted for prying said debris from said surgical surface; and a plane arranged on said tool head, said plane comprising a hole extending through said top surface and said bottom surface, said hole including a wall tapered inwardly from top to bottom, said plane being adapted for scooping said debris from said surgical surface.

15. The ophthalmological surgical instrument of claim 14 wherein said tool head is attached to said handle at an obtuse angle between said top surface and said handle.

16. The ophthalmological surgical instrument of claim 14 wherein said forward distal tip is angled upwardly relative to said top surface of said tool head.

17. The ophthalmological surgical instrument of claim 14 wherein said tool head is made of a transparent material for enabling a user to see said surgical surface under said tool head when said bottom surface of said tool head is positioned flat on said surgical surface.

18. The ophthalmological surgical instrument of claim 14 wherein said V-shaped notch includes a sharply beveled front edge that forms a rear facing blade, said V-shaped notch also includes a rear edge.

19. The ophthalmological surgical instrument of claim 14, further including a measuring scale arranged on said tool head, said scale being adapted for conveniently measuring said debris on said surgical surface.

* * * * *